Figure 1:
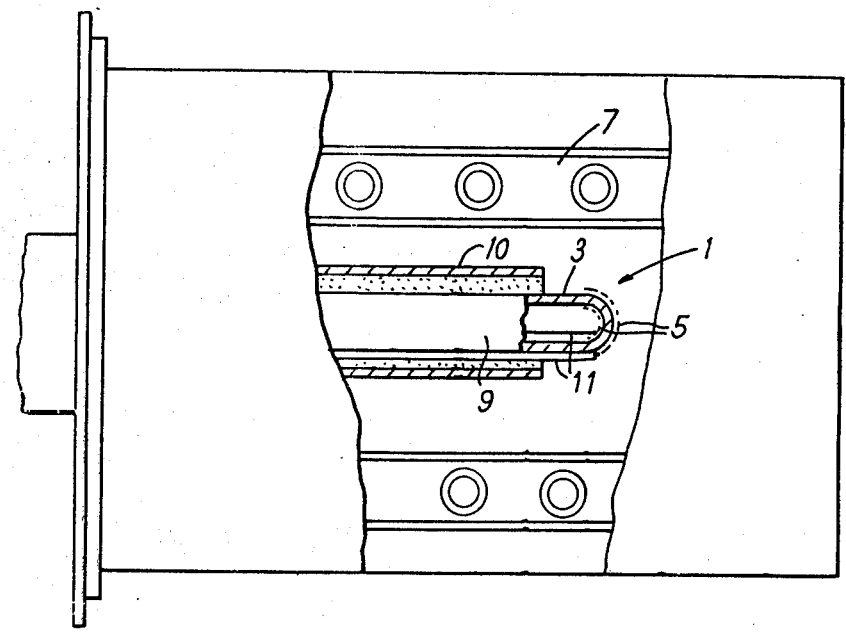

United States Patent [19]
Rudd

[11] 3,998,375
[45] Dec. 21, 1976

[54] BONDING OF METALS TO SOLID ELECTROLYTES

[75] Inventor: Derek Austen Rudd, Pulloxhill, England

[73] Assignee: George Kent Limited, England

[22] Filed: Dec. 5, 1975

[21] Appl. No.: 638,091

[30] Foreign Application Priority Data

Dec. 9, 1974 United Kingdom ............ 53211/74

[52] U.S. Cl. ............................... 228/122; 228/178; 228/208; 204/195 S; 427/205
[51] Int. Cl.² ........................................ G01N 27/30
[58] Field of Search .......... 228/178, 225, 226, 245, 228/246, 248, 253, 254, 903, 122, 123, 208; 427/191, 205; 204/195 S

[56] References Cited

UNITED STATES PATENTS

| | | | |
|---|---|---|---|
| 2,241,095 | 5/1941 | Marvin | 427/191 |
| 2,251,410 | 8/1941 | Koehring | 29/420.5 |
| 3,029,559 | 4/1962 | Treptow | 228/122 X |
| 3,598,635 | 8/1971 | Sagona | 427/191 X |

*Primary Examiner*—Al Lawrence Smith
*Assistant Examiner*—K. J. Ramsey
*Attorney, Agent, or Firm*—Browdy and Neimark

[57] ABSTRACT

A method of bonding metal particles to solid electrolytic material, suitably for making an electrolytic cell for measuring the oxygen content of gases. In a first stage of the method thin, generally flat metal particles are applied to a surface of the electrolyte and bonded to the surface by heating. In a second stage, further metal particles are bonded to the particles applied in the first stage. The further particles are thicker in relation to their other dimensions than are the particles employed in the first stage.

11 Claims, 2 Drawing Figures

BONDING OF METALS TO SOLID ELECTROLYTES

This invention relates to the bonding of metals to solid electrolytic material.

Probes have been proposed for determining the oxygen content of flue gases which rely for their operation on the ability of certain ceramic materials, such as zirconia, to act as solid electrolytes when heated to high temperatures. The materials are insulators at low temperatures but become conductive when heated to high temperatures. Their ability to do so arises from the presence of vacant oxygen sites in the crystal lattice. If the pressure of oxygen in the gas on one side of the material is equal to the pressure of oxygen in the gas on the other side an equilibrium is established at high temperatures between the oxygen in the lattice and the external oxygen. However, if there is a difference between the pressure of oxygen on one side and that on the other side there is a general movement of oxygen ions through the lattice, oxygen being absorbed from the gas with the higher pressure of oxygen and being released into the gas with the lower pressure. The movement of oxygen ions generates an e.m.f. which is detected as a potential difference between electrodes of a noble metal which are provided on respective opposite sides of the material. The magnitude of the potential difference is representative of the difference between the pressures of oxygen in the two gases.

In making the probes referred to above it is desirable to provide a maximum area of contact between each electrode and the electrolytic material and between each electrode and the oxygen in the surrounding atmosphere. At the same time, the electrodes should have a porous structure, which allows ready access of oxygen to the electrolytic material, and they should be firmly bonded to the electrolyte.

The present invention includes a method of bonding metals to solid electrolytic material which comprises applying a first layer comprising thin generally flat metal particles to a surface of the material, heating to bond the metal particles in the layer to the surface, applying to the said metal particles from the first layer a second layer comprising further metal particles, each of the further metal particles having a thickness which is greater in relation to the other dimensions of the particle than is the case for the metal particles from the first layer, and heating to bond the further metal particles in the second layer to the metal particles from the first layer.

Suitably, the metal particles in the first layer have a thickness of approximately 0.5 $\mu$ and other dimensions between 1 $\mu$ and 10 $\mu$. Suitably, the further metal particles in the second layer have dimensions of approximately 10 $\mu$ in each of three mutually perpendicular directions.

Preferably, the first and second layers are each applied in the form of a paste comprising metal particles suspended in a solvent and binder.

The solid electrolytic material may be zirconia or zirconia stabilised with lime or yttria. In this case the metal particles and the further metal particles are preferably platinum.

Preferably, the first layer is heated to a temperature of 1050° C to 1550° C in order to sinter and bond the metal particles to the material. Likewise, the second layer is preferably heated to a temperature of 1050° C–1550° C in order to sinter and bond the further particles to the metal particles from the first layer.

Preferably, heating is effected for a period between 1 and 3 hours.

Figure 2:
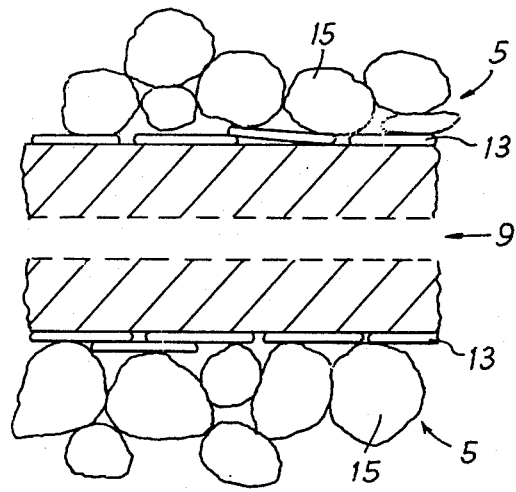

The invention will now be described, by way of example, with reference to the accompanying drawings, in which:

FIG. 1 is a side elevation, partly in section, of an electrolytic cell having electrodes bonded to solid electrolytic material by a method according to the invention; and FIG. 2 is an enlarged sectional view of part of the cell of FIG. 1.

One method according to the invention is used in making a probe for determining the oxygen content of low temperature flue gases. Referring to FIG. 1 of the drawings, the probe includes an electrolytic cell 1 made up of a solid electrolyte 3 contacted on opposite sides thereof by metal electrodes 5. A furnace 7 is provided for heating the cell 1 to a temperature at which the electrolyte 3 has become conductive.

In the present probe the electrolyte 3 is zirconia stabilised with lime and is formed as a short tube 9 which is open at one end and closed at the other. The zirconia tube 9 is mounted in a stainless steel supporting tube 10, which also supports the furnace 7. The electrodes 5 are provided at or near the closed end of the zirconia tube 9 and are connected to external measuring circuits (not shown) via electrical leads 11. A reference gas is supplied to the interior of the zirconia tube 9.

Referring to FIG. 2, each of the electrodes 5 in the present probe is formed by applying a first layer of a paste made up of platinum particles 13 suspended in organic solvents and binders to the inner and outer surfaces of the closed end of the zirconia tube 9. The platinum particles 13 in the paste forming the first layer are generally thin and flat, i.e. flakes, being between 1 $\mu$ and 10 $\mu$ in length, between 1 $\mu$ and 10 $\mu$ in breadth and approximately 0.5 $\mu$ in thickness.

Once the first paste has been applied to the tube 9 it is dried in air and then heated in a furnace and maintained in air at a temperature of 1300° C for 1 hour in order to bond the platinum particles 13 to the zirconia.

The number of platinum particles 13 is sufficiently small for the platinum to be porous, and there may even be breaks so that the particles 13 do not form a continuous electrical conductor.

A second layer of paste is now applied to the platinum particles 13 on each side of the zirconia tube 9. This second paste is also made up of platinum particles suspended in organic solvents and binders, but the particles 15 in the second paste are coarser than the particles 13 in the first paste. Thus, particles 15 may be approximately 10 $\mu$ in length, breadth and thickness.

Once the second paste has been applied it is dried in air and then heated in air to 1300° C for 1 hour to burn off the solvents and binders and to sinter the particles 15 to the particles 13.

It is found that the platinum electrodes 5 formed from particles 13 and 15 are porous and readily allow access of surrounding gases to the zirconia tube 9. On the other hand, the bond between the platinum and the zirconia is strong and forms a good electrical connection.

If the electrodes 5 are formed by a method which employs a single paste containing only flakes of platinum it is found that the electrodes may be impervious to adjacent gases. If a single paste containing only coarse particles of platinum is used it is found that the platinum does not bond well to the zirconia.

The platinum particles 13 can be bonded to the zirconia tube 9 and the particles 15 bonded to the particles 13 at a lower temperature if the heating period is increased. Thus, a bonding temperature of 1050° C is satisfactory if heating is continued for approximately 3 hours.

As an alternative to platinum other noble metals such as an alloy of gold and palladium can be employed. The present method can also be used for bonding base metals and alloys to solid electrolytes. Further, the particles 13 and 15 may be of different but compatible metals.

I claim:

1. A method of bonding metals to solid electrolytic material which comprises applying a first layer comprising thin generally flat metal particles to a surface of the material, heating to bond the metal particles in the first layer to the surface, applying to the said metal particles from the first layer a second layer comprising further metal particles, each of the further metal particles having a thickness which is greater in relation to the other dimensions of the particle than is the case for the metal particles from the first layer, and heating to bond the further metal particles in the second layer to the metal particles from the first layer.

2. A method as claimed in claim 1, wherein the metal particles in the first layer have a thickness of approximately 0.5 $\mu$ and other dimensions between 1 $\mu$ and 10 $\mu$.

3. A method as claimed in claim 2, wherein the further particles in the second layer have dimensions of approximately 10 $\mu$ in each of three mutually perpendicular directions.

4. A method as claimed in claim 1, in which the first layer is applied to the surface of the material in the form of a paste comprising metal particles suspended in a solvent and binder.

5. A method as claimed in claim 1, wherein the second layer is applied in the form of a paste comprising further metal particles suspended in a solvent and binder.

6. A method as claimed in claim 1, wherein the solid electrolytic material is zirconia or zirconia stabilised with lime or yttria.

7. A method as claimed in claim 1, in which the metal particles and the further metal particles are platinum.

8. A method as claimed in claim 7, in which the first layer is heated to a temperature of 1,050° C to 1,500° C in order to sinter and bond the metal particles to the material.

9. A method as claimed in claim 7, in which the second layer is heated to a temperature of 1,050° C to 1,550° C in order to sinter and bond the further particles to the metal particles from the first layer.

10. A method as claimed in claim 8, wherein heating is effected for a period between 1 and 3 hours.

11. A solid electrolytic material having a metal bonded thereto by the method as claimed in claim 1.

* * * * *